(12) United States Patent
Marczyk

(10) Patent No.: US 8,074,858 B2
(45) Date of Patent: Dec. 13, 2011

(54) SURGICAL RETRACTION MECHANISM

(75) Inventor: Stanislaw Marczyk, Stratford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 241 days.

(21) Appl. No.: 12/476,327

(22) Filed: Jun. 2, 2009

(65) Prior Publication Data
US 2010/0012702 A1    Jan. 21, 2010

Related U.S. Application Data

(60) Provisional application No. 61/081,456, filed on Jul. 17, 2008.

(51) Int. Cl.
*A61B 17/068* (2006.01)
(52) U.S. Cl. .................... 227/175.1; 227/19; 606/219
(58) Field of Classification Search .... 227/175.1–182.1, 227/19; 606/219
See application file for complete search history.

(56) References Cited

U.S. PATENT DOCUMENTS

| | | | |
|---|---|---|---|
| 4,508,523 A | 4/1985 | Leu | |
| 5,143,453 A | 9/1992 | Weynant nee Girones | |
| 5,207,697 A | 5/1993 | Carusillo et al. | |
| 5,223,663 A | 6/1993 | Bender-Zanoni et al. | |
| 5,307,976 A * | 5/1994 | Olson et al. ................ | 227/175.3 |
| 5,350,355 A | 9/1994 | Sklar | |
| 5,383,880 A | 1/1995 | Hooven | |
| 5,467,911 A | 11/1995 | Tsuruta et al. | |
| 5,518,163 A | 5/1996 | Hooven | |
| 5,518,164 A | 5/1996 | Hooven | |
| 5,667,517 A | 9/1997 | Hooven | |
| 5,954,259 A | 9/1999 | Viola et al. | |
| 5,980,548 A | 11/1999 | Evans et al. | |
| 6,017,354 A | 1/2000 | Culp et al. | |
| 6,090,123 A | 7/2000 | Culp et al. | |
| 6,126,651 A | 10/2000 | Mayer | |
| 6,231,565 B1 | 5/2001 | Tovey et al. | |
| 6,264,086 B1 | 7/2001 | McGuckin, Jr. | |
| 6,264,087 B1 | 7/2001 | Whitman | |
| 6,295,330 B1 | 9/2001 | Skog et al. | |
| 6,315,184 B1 | 11/2001 | Whitman | |
| 6,329,778 B1 | 12/2001 | Culp et al. | |
| 6,443,973 B1 | 9/2002 | Whitman | |
| 6,505,768 B2 | 1/2003 | Whitman | |

(Continued)

FOREIGN PATENT DOCUMENTS

EP    1520521    4/2005

(Continued)

OTHER PUBLICATIONS

European Search Report for corresponding EP 09251811 date of mailing is Nov. 11, 2009 (3 pages).

(Continued)

*Primary Examiner* — Lindsay Low

(57) ABSTRACT

A retraction mechanism has been developed for use with a hand held surgical apparatus. The retraction mechanism includes a motor, a first speed reducing mechanism, a clutch mechanism incorporating a second speed reducing mechanism, and a shaft. The first speed reducing mechanism is configured to be driven by a motor. The second speed reducing mechanism has a locked state and an unlocked state. In addition, the clutch mechanism is disposed in mechanical cooperation with the first speed reducing mechanism. The shaft is configured to rotate upon activation of the motor the second speed reducing mechanism is in the locked state. The rotation of the shaft retracts a firing drive of the hand held surgical apparatus.

16 Claims, 8 Drawing Sheets

U.S. PATENT DOCUMENTS

| | | | | |
|---|---|---|---|---|
| 6,514,247 B1 | * | 2/2003 | McGaffigan et al. | 606/41 |
| 6,517,565 B1 | * | 2/2003 | Whitman et al. | 606/219 |
| 6,533,157 B1 | | 3/2003 | Whitman | |
| 6,698,643 B2 | | 3/2004 | Whitman | |
| 6,716,233 B1 | | 4/2004 | Whitman | |
| 6,843,403 B2 | | 1/2005 | Whitman | |
| 6,846,307 B2 | | 1/2005 | Whitman et al. | |
| 6,846,308 B2 | | 1/2005 | Whitman et al. | |
| 6,846,309 B2 | | 1/2005 | Whitman et al. | |
| 6,849,071 B2 | | 2/2005 | Whitman et al. | |
| 6,905,057 B2 | | 6/2005 | Swayze et al. | |
| 6,959,852 B2 | | 11/2005 | Shelton et al. | |
| 6,979,328 B2 | | 12/2005 | Baerveldt et al. | |
| 6,981,941 B2 | | 1/2006 | Whitman et al. | |
| 7,000,819 B2 | | 2/2006 | Swayze et al. | |
| 7,032,798 B2 | | 4/2006 | Whitman et al. | |
| 7,059,508 B2 | | 6/2006 | Shelton, IV et al. | |
| 7,077,856 B2 | | 7/2006 | Whitman | |
| 7,083,075 B2 | | 8/2006 | Swayze et al. | |
| 7,128,254 B2 | | 10/2006 | Shelton et al. | |
| 7,143,926 B2 | | 12/2006 | Shelton, IV et al. | |
| 7,159,750 B2 | * | 1/2007 | Racenet et al. | 227/180.1 |
| 7,364,061 B2 | | 4/2008 | Swayze et al. | |
| 7,422,136 B1 | | 9/2008 | Marczyk | |
| 7,431,188 B1 | * | 10/2008 | Marczyk | 227/175.1 |
| 7,464,846 B2 | | 12/2008 | Shelton, IV et al. | |
| 7,556,185 B2 | * | 7/2009 | Viola | 227/175.1 |
| 2002/0025891 A1 | | 2/2002 | Colosky et al. | |
| 2002/0165541 A1 | | 11/2002 | Whitman | |
| 2003/0073981 A1 | | 4/2003 | Whitman et al. | |
| 2004/0094597 A1 | | 5/2004 | Whitman et al. | |
| 2004/0232201 A1 | | 11/2004 | Wenchell et al. | |
| 2005/0067458 A1 | | 3/2005 | Swayze et al. | |
| 2005/0070958 A1 | | 3/2005 | Swayze et al. | |
| 2005/0131390 A1 | | 6/2005 | Heinrich et al. | |
| 2005/0178813 A1 | | 8/2005 | Swayze et al. | |
| 2005/0187576 A1 | | 8/2005 | Whitman et al. | |
| 2005/0192609 A1 | | 9/2005 | Whitman et al. | |
| 2005/0228341 A1 | | 10/2005 | Edgerley | |
| 2006/0151567 A1 | | 7/2006 | Roy | |
| 2006/0175375 A1 | | 8/2006 | Shelton, IV | |
| 2006/0278680 A1 | | 12/2006 | Viola et al. | |
| 2007/0023476 A1 | | 2/2007 | Whitman et al. | |
| 2007/0023477 A1 | | 2/2007 | Whitman et al. | |
| 2007/0102473 A1 | | 5/2007 | Shelton, IV et al. | |
| 2007/0175947 A1 | | 8/2007 | Ortiz et al. | |
| 2007/0175949 A1 | | 8/2007 | Shelton, IV et al. | |
| 2007/0175951 A1 | | 8/2007 | Shelton, IV et al. | |
| 2007/0175952 A1 | | 8/2007 | Shelton, IV | |
| 2007/0175953 A1 | | 8/2007 | Shelton, IV | |
| 2007/0175955 A1 | | 8/2007 | Shelton, IV et al. | |
| 2007/0175956 A1 | | 8/2007 | Swayze et al. | |
| 2007/0175957 A1 | | 8/2007 | Shelton, IV | |
| 2007/0175958 A1 | | 8/2007 | Shelton, IV | |
| 2007/0175959 A1 | | 8/2007 | Shelton, IV | |
| 2007/0175960 A1 | | 8/2007 | Shelton, IV et al. | |
| 2007/0175962 A1 | | 8/2007 | Shelton, IV et al. | |
| 2007/0175964 A1 | | 8/2007 | Shelton, IV et al. | |
| 2007/0191865 A1 | * | 8/2007 | Pappas | 606/108 |
| 2008/0029570 A1 | | 2/2008 | Shelton et al. | |
| 2008/0029571 A1 | | 2/2008 | Shelton et al. | |
| 2008/0029572 A1 | | 2/2008 | Shelton et al. | |
| 2008/0029573 A1 | | 2/2008 | Shelton et al. | |
| 2008/0029574 A1 | | 2/2008 | Shelton et al. | |
| 2008/0029575 A1 | | 2/2008 | Shelton et al. | |
| 2008/0029576 A1 | | 2/2008 | Shelton et al. | |
| 2008/0029577 A1 | | 2/2008 | Shelton et al. | |
| 2008/0164296 A1 | | 7/2008 | Shelton et al. | |
| 2009/0045242 A1 | * | 2/2009 | Viola | 227/177.1 |

FOREIGN PATENT DOCUMENTS

| | | |
|---|---|---|
| EP | 1690502 | 8/2006 |
| EP | 1 813 203 A | 8/2007 |
| EP | 1813202 | 8/2007 |
| EP | 1813205 | 8/2007 |
| EP | 1872727 | 1/2008 |
| EP | 1980214 | 10/2008 |
| WO | WO 97/29694 | 8/1997 |
| WO | WO 2004/032760 A2 | 4/2004 |
| WO | WO2007/142625 | 12/2007 |

OTHER PUBLICATIONS

European Search Report for corresponding EP 092516993 date of mail is Nov. 5, 2009 (3 pages).

* cited by examiner

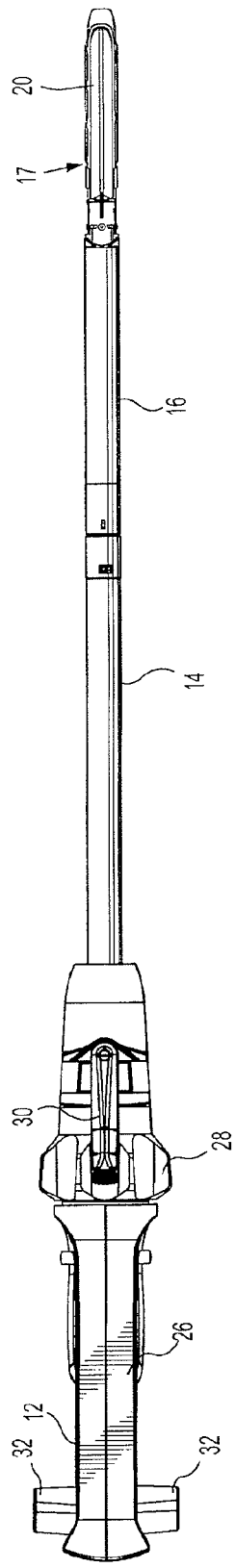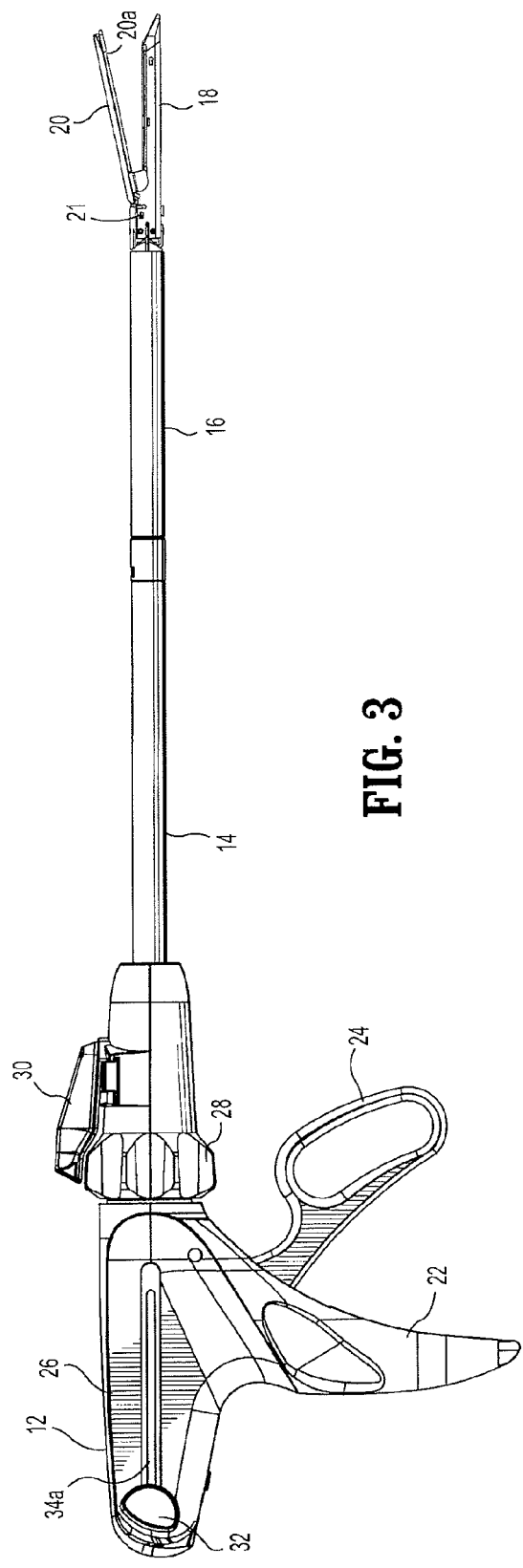
FIG. 2
FIG. 3

SURGICAL RETRACTION MECHANISM

CROSS REFERENCE TO RELATED APPLICATION

The present application claims the benefit of and priority to U.S. Provisional Application Ser. No. 61/081,456 filed on Jul. 17, 2008, the entire contents of which are incorporated herein by reference

BACKGROUND

1. Technical Field

The present disclosure relates to hand held surgical stapling apparatus. More particularly, the present disclosure relates to retraction mechanism for hand held surgical stapling apparatus.

2. Background of Related Art

Some surgical apparatus are capable of fastening tissue layers. In general, surgical fastening apparatus include two elongated jaw members designed for capturing or clamping tissue. One jaw member typically contains a staple cartridge. The staple cartridge houses a plurality of staples. Typically, the staple cartridges include at least two lateral rows of retention slots. Each retention slot is adapted to receive a staple. The other jaw member has an anvil that defines a surface for forming the staple legs as the staples are driven from the staple cartridge. The stapling operation is usually effected by cam members that translate through the staple cartridge. These cam members are connected to a firing drive that moves from a proximal position to a distal position when a user actuates the surgical stapling apparatus. Upon actuation of the surgical stapling apparatus, the firing drive moves in a distal direction and causes the cam members to move from a proximal position to a distal position through the staple cartridge. While the cam members translate through the staple cartridge, these cam members sequentially act on staple pushers positioned along the staple cartridge to eject the staples from the staple cartridge. The surgical stapling apparatus may further include a knife operatively attached to the cam members and positioned between two rows of staple slots. Alternatively, the knife may be attached to the drive member rather than the cam member. Since the knife is operatively attached to the cam members, the knife moves from proximal position to a distal position, while the cam members translate from a proximal portion to a distal portion of the staple cartridge. As the knife moves through the staple cartridge, it cuts or opens tissue positioned between the jaw members.

Another surgical stapling apparatus applies a double row of staples on each side of the incision. This surgical stapling apparatus has a disposable loading unit wherein a cam member moves from a proximal position to a distal position through an elongate guide path between two sets of staggered staple carrying grooves. Staple drive members are located within the grooves and are positioned in such a manner so as to be contacted by the longitudinally moving cam member. The staple members eject the staples in the staple cartridge as the cam member moves axially along the elongate guide path.

Each of the apparatus described hereinabove is designed for use in conventional surgical procedures wherein surgeons have direct manual access to the operative site. In endoscopic or laparoscopic procedures, however, surgery is performed through a small incision or through a narrow cannula inserted through small entrance wounds in the skin. Endoscopic surgical stapling devices have been developed to address the specific needs of endoscopic and laparoscopic surgical procedures. A few examples of endoscopic surgical stapling devices are disclosed in U.S. Pat. No. 5,307,976; U.S. Pat. No. 5,312,023; U.S. Pat. No. 5,326,013; U.S. Pat. No. 5,332,142; and U.S. Pat. No. 6,241,139, the entire contents of each of which are incorporated herein by reference.

As discussed above, the cam members of the surgical stapling apparatus discussed above are operatively connected to a firing drive. Consequently, a distal motion of the firing drive causes the cam members to move in a distal direction. The surgical stapling apparatus devices discussed above may further include a retraction mechanism to return the firing drive to a proximal position. Given that the cam members are coupled to the firing drive, the retraction mechanism also moves the cam members (along with the firing drive) to a proximal position. The retraction mechanism includes a pair of retractor knobs movably positioned along a barrel portion of a handle assembly. The retraction knobs are manually pulled proximally to return the firing drive to its proximal position after firing the surgical stapling apparatus.

Other endoscopic stapling apparatus include powered retraction mechanisms. For instance, U.S. patent application Ser. No. 11/784,804, filed Apr. 9, 2007, the entire contents of which is hereby incorporated by reference, discloses a surgical stapling apparatus including a powered retraction mechanism. An embodiment of this retraction mechanism includes a motor operatively associated with a pulley and a slip clutch. The pulley is configured to retract the firing drive of the surgical stapling apparatus once the slip clutch moves to its engaged position.

The surgical apparatus described above have provided significant clinical benefits. Nonetheless, improvements to these instruments are possible. For instance, it would be beneficial to provide a more compact retraction mechanism for surgical apparatus.

SUMMARY

The present disclosure relates to a retraction mechanism for use with a hand held surgical apparatus. An embodiment of the presently disclosed retraction mechanism includes a motor, a first speed reducing mechanism, a clutch mechanism incorporating a second speed reducing mechanism, and a shaft. The first speed reducing mechanism is adapted to be driven by the motor. The second speed reducing mechanism has a locked state and an unlocked state. The clutch mechanism is disposed in mechanical cooperation with the first speed reducing mechanism. The shaft is configured to rotate upon activation of the motor when the second speed reducing mechanism is in the locked state. In operation, a rotation of the shaft retracts a firing drive of a surgical apparatus. In one embodiment, the second speed reducing mechanism is a planetary clutch.

In an alternative embodiment, the retraction mechanism includes a motor, a speed reducing mechanism, a planetary clutch, and a firing drive. The motor is disposed in electromechanical cooperation with a speed reducing mechanism. The planetary clutch has a locked state and an unlocked state. Additionally, the planetary clutch is operatively coupled to the speed reducing mechanism. The firing drive is adapted to actuate a surgical tool. Moreover, the firing drive is adapted to move proximally in response to a rotation of a shaft driven by the planetary clutch while in the locked state. The shaft rotates upon activation of the motor.

BRIEF DESCRIPTION OF THE DRAWINGS

Various embodiments of the presently disclosed surgical apparatuses and retraction mechanism are described herein with reference to the drawings:

FIG. 2 is a top view of the surgical apparatus of FIG. 1;

FIG. 3 is a side elevational view of the surgical apparatus of FIG. 1;

DETAILED DESCRIPTION OF THE DRAWINGS

Figure 1:
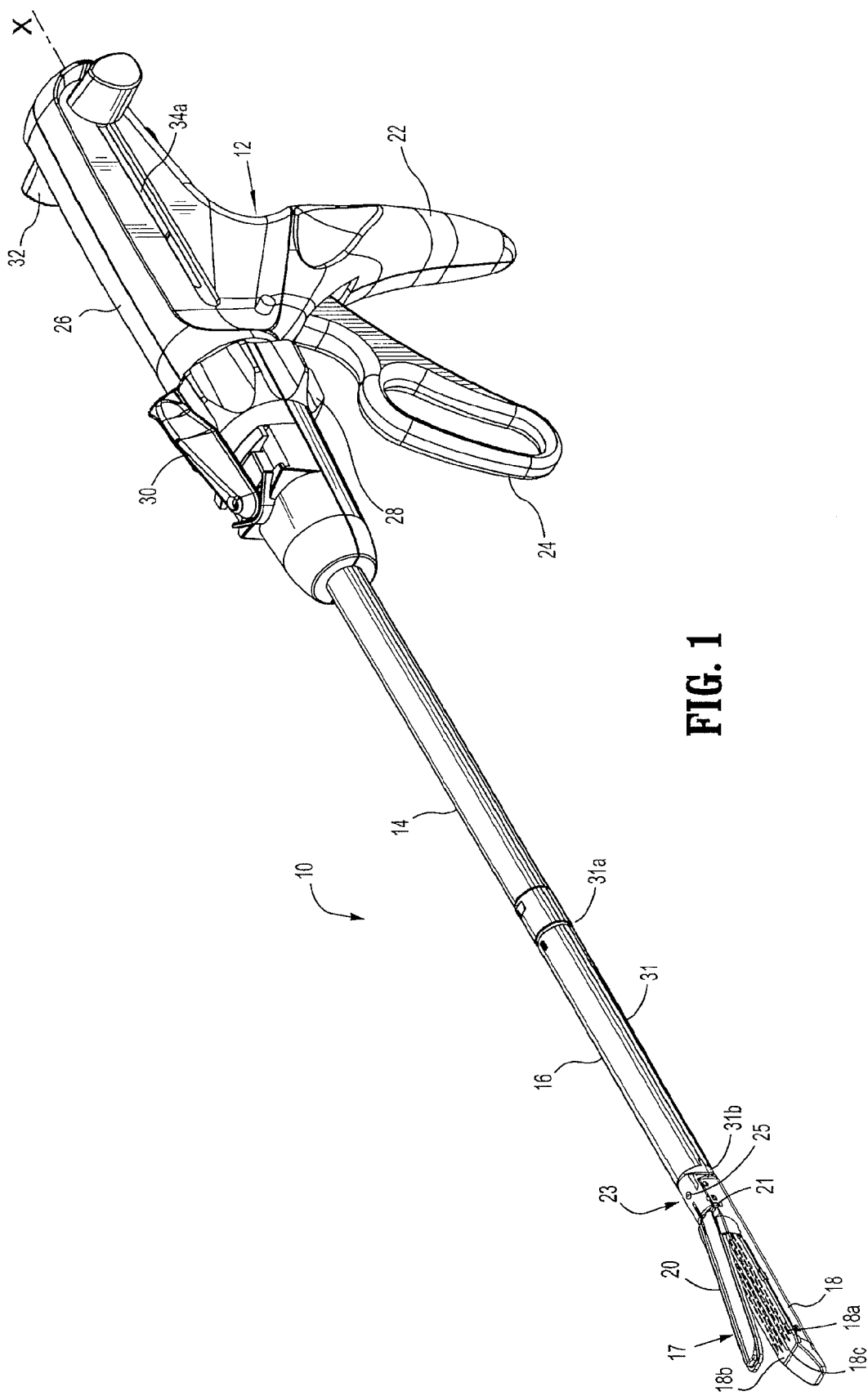
FIG. 1 is a perspective view of a surgical apparatus according to an embodiment of the present disclosure.

Embodiments of the presently disclosed surgical apparatus and retraction mechanism for use therewith will now be described in detail with reference to the drawings in which like reference numerals designate identical or similar elements in each of the several views. In the description and in the claims, the term "proximal," as is traditional, will refer to the end of the apparatus, or a portion thereof, that is closest to the operator, while the term "distal," will refer to the end of the apparatus, or a portion thereof, that is farthest from the operator. In addition, the singular forms, such as "a," "an," and "the," include the plural form. Likewise, all plural forms include the singular form, unless clearly stated otherwise.

With reference to FIGS. 1-3, an embodiment of the presently disclosed surgical apparatus is generally designated as 10. In the interest of brevity, this disclosure will focus primarily on systems, methods and structures for returning a firing drive of surgical apparatus 10 to its retracted or proximal position. U.S. Pat. No. 6,953,139, the entire disclosure of which is incorporated herein by reference, contains a detailed discussion of the remaining components and methods of use of surgical apparatus 10.

Surgical apparatus 10 is an endoscopic or laparoscopic instrument including a handle assembly 12 and an elongated body 14 extending therefrom. A single use loading unit ("SULU") 16 is releasably secured to a distal end of elongated body 14. Although the drawings show SULU 16, one skilled in the art will recognize that any other suitable tool or end effector can be releasably secured to elongated body 14. In particular, SULU 16 includes an elongate portion 31 disposed in mechanical cooperation with elongate body 14. Specifically, a proximal end 31a of the elongate portion 31 is operatively connected to elongated body 14. In turn, a distal end 31b of elongate portion 31 is coupled to a tool assembly 17 of SULU 16.

Tool assembly 17 includes a cartridge assembly 18 adapted to retain a plurality of surgical staples in retention slots 18a. Retention slots 18a are arranged in rows that extend along a tissue contacting surface 18b. These rows of retention slots 18a correspond to rows of staples. While retention slots 18a may be arranged in numerous ways, an embodiment of the present disclosure includes retention slots 18a positioned on both sides of a knife channel 18c disposed on tissue contacting surface 18b. Knife channel 18c extends longitudinally along tissue contacting surface 18b and is adapted to receive a knife therealong. In operation, a knife slides through knife channel 18c during or after stapling.

Aside from cartridge assembly 18, tool assembly 17 has an anvil assembly 20. Anvil assembly 20 includes a tissue contacting surface 20a adapted to deform staples during the stapling process. In addition, anvil assembly 20 includes a pivot pin 21. Pivot pin 21 or any other suitable fastening device, such as a hinge, pivotably connects anvil assembly 20 and cartridge assembly 18 at their respective proximal ends. The pivot pin 21 facilitates movement of anvil assembly 20 between an open position spaced from cartridge assembly 18 and an approximated or clamped position in juxtaposed alignment with cartridge assembly 18. The relative motion of anvil assembly 20 with respect to cartridge assembly 18 allows the actuation of SULU 16 to clamp and immobilize tissue.

Altogether, SULU 16 is configured to apply at least one row of staples. SULUs 16 may have various staple line lengths and configurations. In some embodiments, SULUs 16 have staple line lengths measuring from about 30 mm to 60 mm in length. In addition to staple line length, other features of SULU 16 can adjust to the different needs depending on the circumstances.

For example, SULU 16 may include a tool assembly 17 pivotable about its proximal end, as disclosed in U.S. Pat. No. 6,953,139, the disclosure of which is hereby incorporated by reference. In this embodiment, a user controls the pivotable movement of tool assembly 17 through an articulation lever 30 positioned on handle assembly 12. Articulation lever 30 is pivotably engaged to a cam member (not shown) positioned inside handle assembly 12. The cam member, in turn, is operatively coupled to a translation member (not shown). The translation member is positioned within handle assembly 12, and the engagement between the cam member and the translation member inhibits rotation of the translation member, but allows linear movement of the translation member in response to a pivotal movement of articulation lever 30. A distal end of the translation member is coupled to a proximal end of a first articulation link (not shown). During operation, a linear motion of the translation member causes a corresponding linear movement of the first articulation link. The first articulation link, which is mainly located within handle assembly 12, is operatively connected to a second articulation link (not shown). The second articulation link is configured to move linearly in response to a linear movement of the first articulation link and is engaged to a laterally offset inner portion of a mounting assembly 23. Mounting assembly 23 includes a pivot pin 25 and pivotably interconnects tool assembly 17 and elongate portion 31. Since the second articulation link is laterally offset from pivot pin 25, a linear movement of the second articulation links causes mounting assembly 23 to pivot about pivot pin 25 to articulate tool assembly 17.

In addition to controlling the pivoting motion of tool assembly 17, handle assembly 12 directs the actuation of tool assembly 17. To this end, handle assembly 12 includes a stationary handle member 22, a movable handle member 24, and a barrel portion 26 defining a longitudinal axis "X."

Barrel portion 26 has a rotatable member 28 mounted on a distal portion thereof. In use, rotatable member 28 facilitates rotation of elongated body 14 with respect to handle assembly 12.

With reference to FIGS. 4, 4A-4C, and 5, barrel portion 26 encloses a firing drive 2 including a toothed rack 38 and a driving pawl 44. Driving pawl 44 includes a mounting portion 44a and an engagement portion 44b adapted to engage toothed rack 38. A pivot pin 51 pivotably interconnects one end of movable handle member 24 (FIG. 1) and driving pawl 44 and allows engagement portion 44a of driving pawl 44 to pivot toward toothed rack 38 in response to a movement of movable handle member 24 toward stationary handle member 22. Consequently, driving pawl 44 is mounted to selectively engage toothed rack 38 and advance firing drive 2 in a distal direction in response to manipulation of movable handle member 24 (see FIG. 1) through an actuating stroke. A biasing member 47, which may be a torsion spring, is positioned to urge an engagement portion 44b of driving pawl 44 toward toothed rack 38. The mounting portion 44a of pawl 44 is adapted to interact with an abutment wall 45 mounted within barrel portion 26. As discussed above, movable handle member 24 is pivotably connected to pawl 44 so that it is capable of moving engagement portion 44b of driving pawl 44 into contact with toothed rack 38 to advance the firing drive 2 linearly in the distal direction. As a consequence, driving pawl 44 is rotated in and out of engagement with the toothed rack 38 of firing drive 2 upon manipulation of movable handle member 24. Firing drive 2 is operatively connected to a control rod (not shown). The control rod, which is adapted to move linearly in response to a linear motion of firing drive 2, is operatively coupled to a cam roller (not shown) disposed in mechanical cooperation with a anvil assembly 20. The cam rollers are configured to move in a distal direction along a portion of anvil assembly 20 when the control rod is moved distally. When the cam rollers move in distal direction along anvil assembly 20, anvil assembly 20 pivots about pivot pin 21 toward cartridge assembly 18 (See FIGS. 1-3). The control rod is also operatively connected to a cam member (not shown) configured to urge the staples out of the cartridge assembly 18. In operation, the cam members move from a proximal position to a distal position in response to a distal motion of the control rod. As the cam members move distally, the cam members act on staple pushers (not shown) and eject the staples resting on those staple pushers. While ejecting from cartridge assembly 18, the staples exit from cartridge assembly 18 through retention slots 18a and move toward the anvil assembly 20 to staple tissue.

In operation, a user fires surgical apparatus 10 by pivoting movable handle member 24 toward stationary handle 22 against the bias of torsion spring 47 to move driving pawl 44 into engagement with toothed rack 38 on firing drive 2. Consequently, the pivotal motion of movable handle member 24 causes driving pawl 44 to engage toothed rack 28 and drives firing drive 2 distally. The distal advancement of firing drive 2 causes the control rod to move distally. When the control rod moves distally, the cam members move along anvil assembly 20 and urge anvil assembly 20 toward cartridge assembly 18 to clamp tissue positioned between anvil assembly 20 and cartridge assembly 18. The distal movement of the control rod also causes the cam members to move in distal direction. When the cam members move distally, the cam members move the staple pushers toward the anvil assembly 20. Since the staples seat on the staple pushers, the staples are ejected from the cartridge assembly 18 when the staple pushers move toward anvil assembly 20.

In one embodiment, to complete the staple firing operation, movable handle member 24 is once again approximated toward stationary handle 22, causing driving pawl 44 to engage toothed rack 38 and advance firing drive 2 in a distal direction another 15 mm. Thus, in this embodiment, two complete strokes of actuation handle 24 advance firing drive 2 thirty (30) mm within barrel portion 26, causing the sequential ejection of all the surgical staples in cartridge assembly 18. If desired, the operator can incrementally advance firing drive 2 by multiple short strokes, wherein the minimum advancement is dictated by the linear distance between the teeth on rack 38. Therefore, while two complete strokes of a stroke distance of 15 mm may be used to fire a 30 mm disposable loading unit, complete strokes are not necessary or required. Surgical apparatus 10 may be configured to have various stroke distances.

Figure 4:
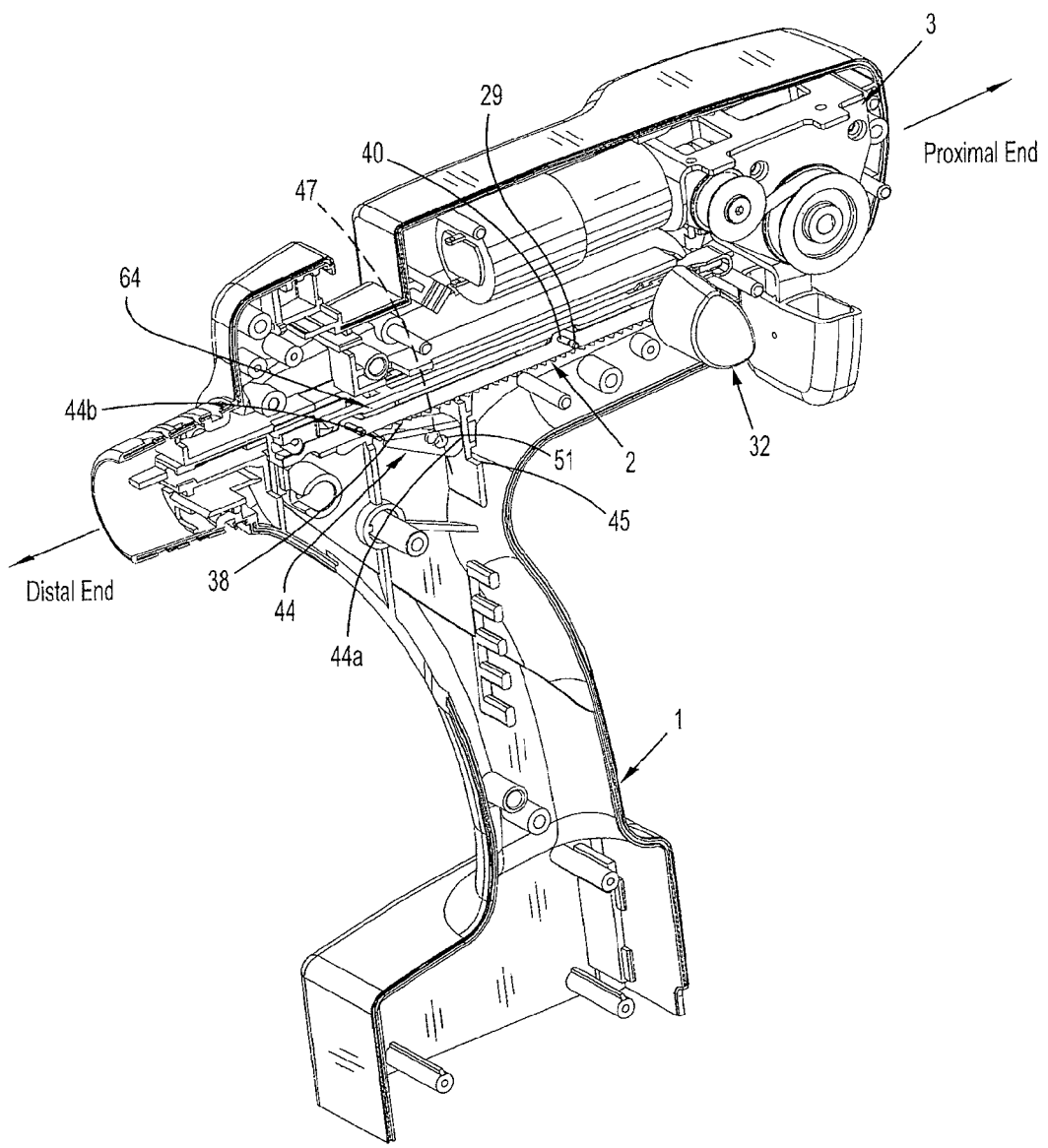
FIG. 4 perspective cross-sectional view of a handle assembly of a surgical apparatus according to an embodiment of the present disclosure.
Figure 4A:
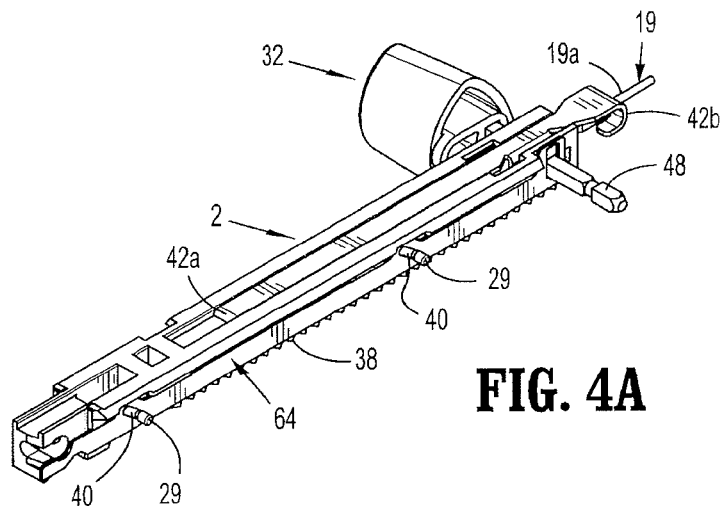
FIG. 4A is a perspective view of a firing drive of the handle assembly of FIG. 4
Figure 4B:
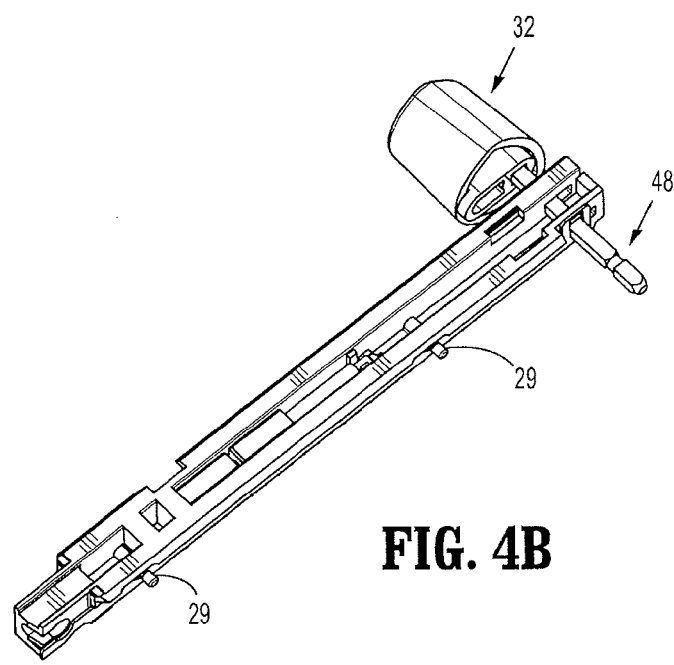
FIG. 4B is a perspective view of the firing drive of the handle assembly of FIG. 4.
Figure 4C:
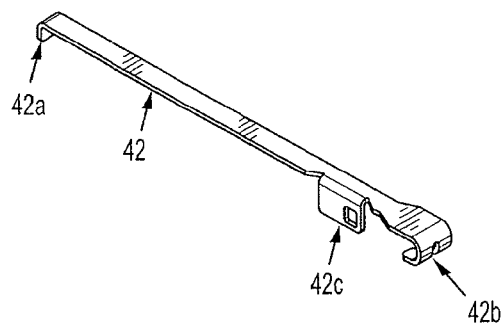
FIG. 4C is perspective view of a connector of the handle assembly of FIG. 4.
Figure 5:
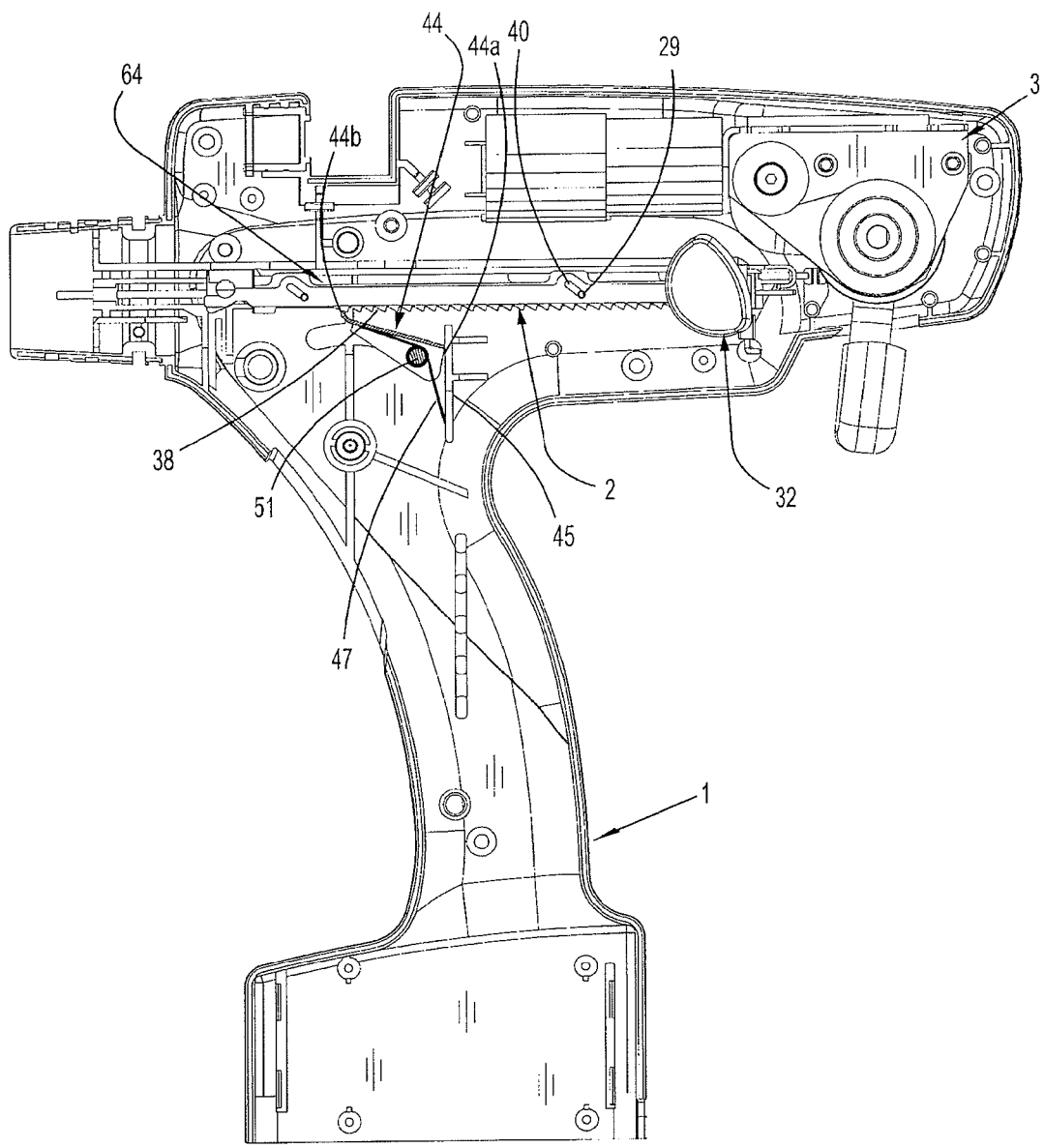
FIG. 5 is side cross-sectional view of the handle assembly of FIG. 4.

A pair of retractor knobs 32 is connected to a proximal end of firing drive 2. A coupling pin 48 interconnects both retraction knobs 32 and facilitates translation of retractor knobs 32 along barrel portion 26. Specifically, at least a portion of coupling pin 48 is dimensioned and configured to translate within a pair of longitudinal slots 34a formed along barrel portion 26, as seen in FIG. 1. A release plate 64 is operatively associated with firing drive 2 and is mounted for movement with respect thereto in response to manipulation of retractor knobs 32. A pair of spaced apart pins 29 extends outwardly from a lateral face of firing drive 2 to engage a pair of corresponding angled cam slots 40 formed in release plate 64, as shown in FIG. 4A. U.S. Pat. No. 7,044,353, the disclosure of which is hereby incorporated by reference herein, describes in detail the structure and manual operation of the firing drive 2 and release plate 64. In brief, a user manually translates retractor knobs 32 in a proximal direction to retract firing drive 2 to its proximal position. As firing drive 2 moves proximally, the cam members operatively associated with to firing drive 2 also move proximally.

Figure 11:
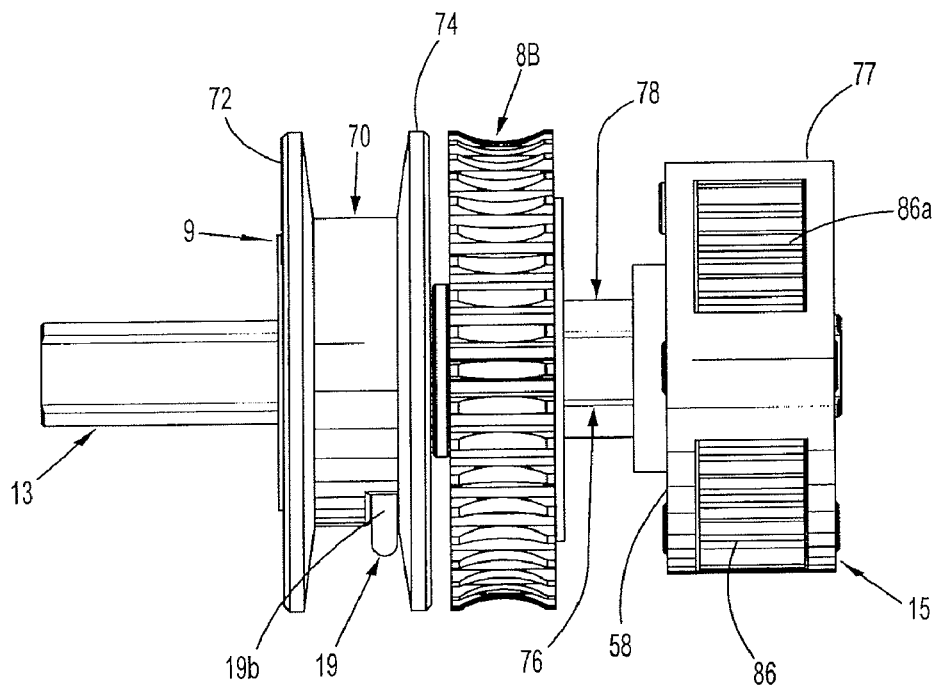
FIG. 11 is front elevational view of a portion of the retraction mechanism of FIG. 6.

To enable retraction, firing drive 2 includes a distally biased connector 42 having distal and proximal ends 42a, 42b. Connector 42 is mounted on a top portion of firing drive 2 and has a hole 42c dimensioned and configured for receiving coupling pin 48. A flexible member 19 interconnects connector 42 and a retraction pulley 9. The present disclosure envisions that flexible member 19 can be a cable, a chain, or any other suitable device capable of interconnecting connector 42 and retraction pulley 9. In particular, a first end 19a of flexible member 19 is attached to the proximal end 42b of connector 42. A second end 19b of flexible member 19 is attached to retraction pulley 9, as seen in FIG. 11.

Referring to FIGS. 5-9, retraction mechanism 3 is generally positioned in parallel with longitudinal axis "X" within handle assembly 12 and facilitates retraction of firing drive 2 to a proximal position. To this end, retraction mechanism 3 is operatively associated with firing drive 2 through flexible member 19. In addition, retraction mechanism 3 includes a motor 6, and optionally a gearbox 6a, disposed in electromechanical cooperation with a speed reducing mechanism or transmission 8. Particularly, a transmission shaft 46 is mounted to motor 6. A coupling 7 interconnects transmission shaft 46 and speed reducing mechanism 8. Speed reducing mechanism 8 effectively reduces the rotational motion supplied by motor 6. In one embodiment, speed reducing mechanism 8 is a worm gear set that includes a first gear 8a configured to mesh with a second gear 8b. First gear 8a is secured to coupling 7 and, in operation, rotates in response to a rotation of transmission shaft 46. In turn, the rotation of first gear 8a causes the rotation of second gear 8b.

Referring to FIGS. 8-11, second gear 8b is rotatably connected to a hollow shaft 78. Hollow shaft 78 is adapted to rotate upon rotation of second gear 8b. Further, hollow shaft 78 has a bore 76 extending therethrough. Bore 76 is adapted to receive at least a portion of a shaft 13. Hollow shaft 78 operatively connects second gear 8b and a clutch mechanism 11. Therefore, clutch mechanism 11 is disposed in rotational cooperation with speed reducing mechanism 8. In the depicted embodiment, clutch mechanism 11 is a planetary clutch. The present disclosure, however, envisions that clutch mechanism 11 may be any other suitable clutch. Clutch mechanism 11 has a locked and an unlocked state. A strap 62 and a spring loaded lever 5 (FIGS. 6 and 7) are designed to work together to switch clutch mechanism 11 from a locked state to an unlocked state and vice versa.

Figure 6:
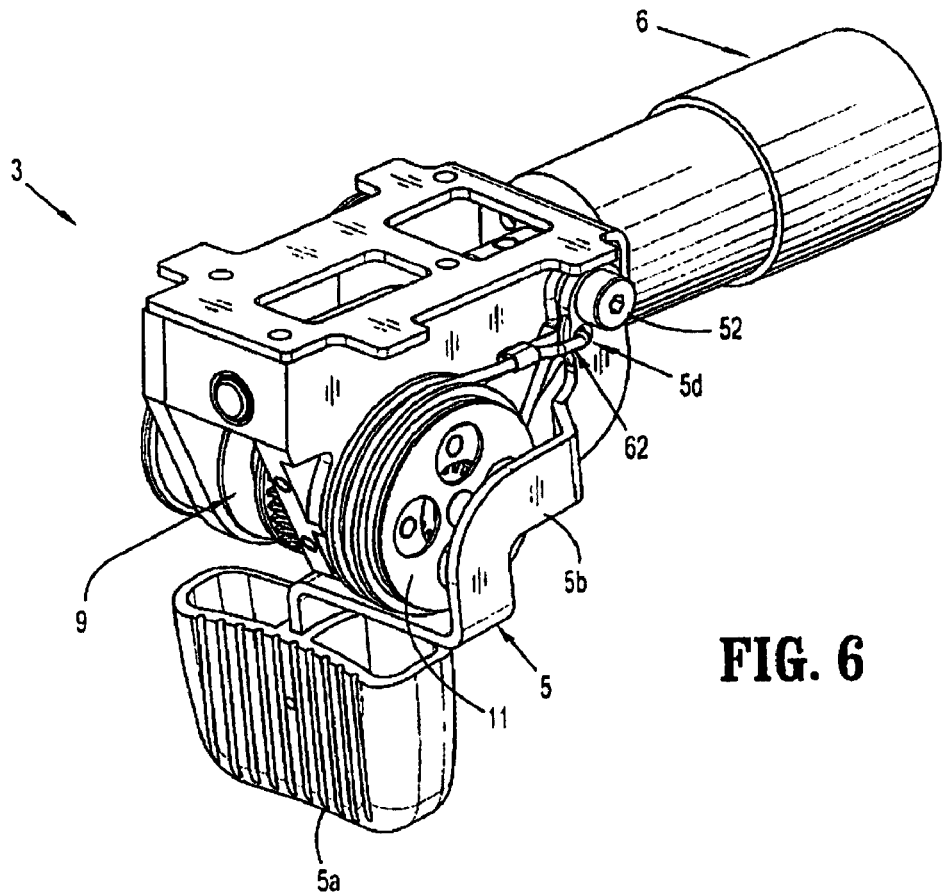
FIG. 6 is a perspective view of a retraction mechanism operatively associated with a lever in accordance with an embodiment of the present disclosure.
Figure 7:
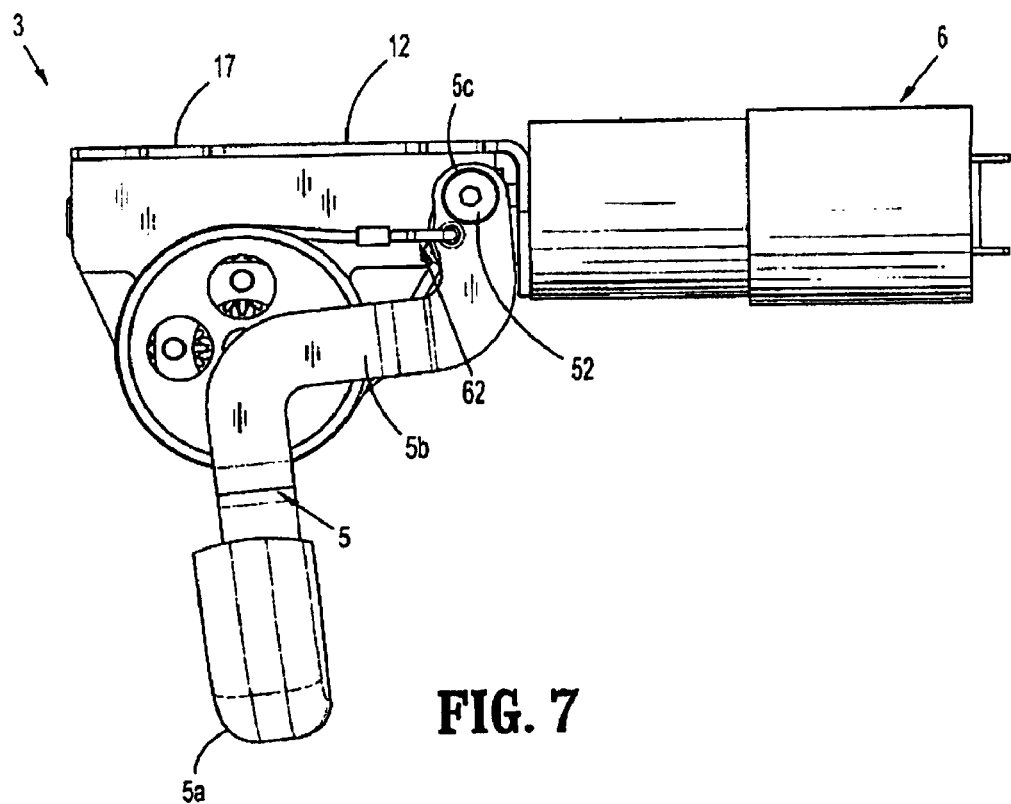
FIG. 7 is a side elevational view of the retraction mechanism and lever of FIG. 6.
Figure 8:
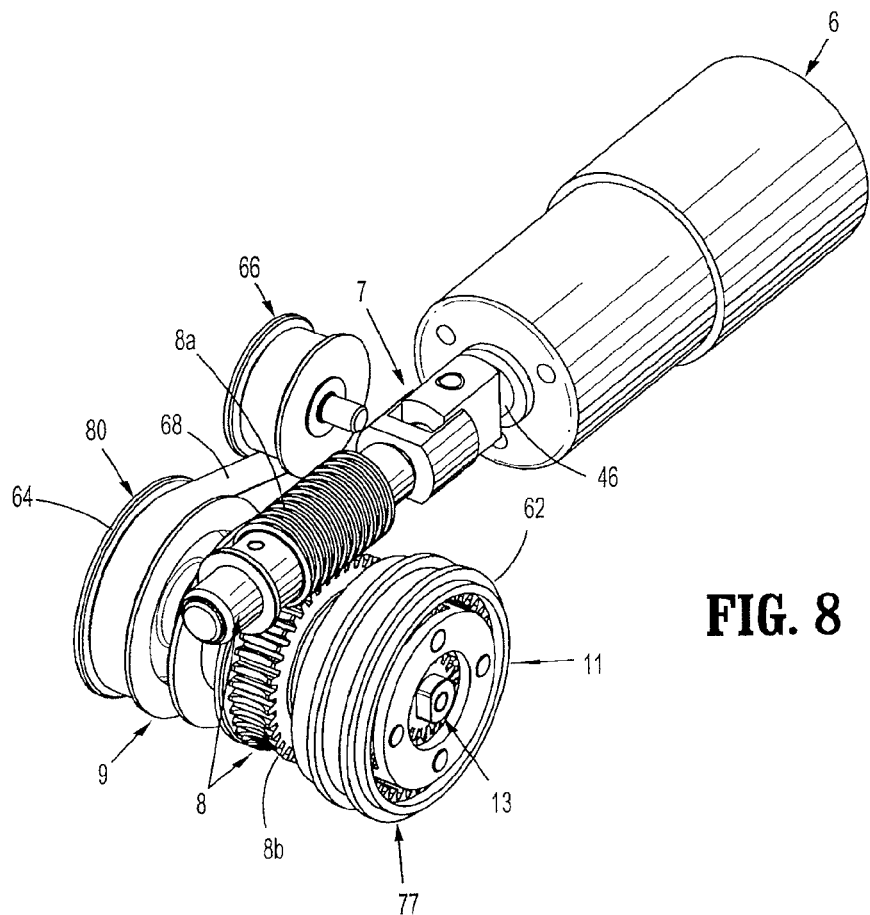
FIG. 8 is a perspective view of the retraction mechanism of FIG. 6.
Figure 9:
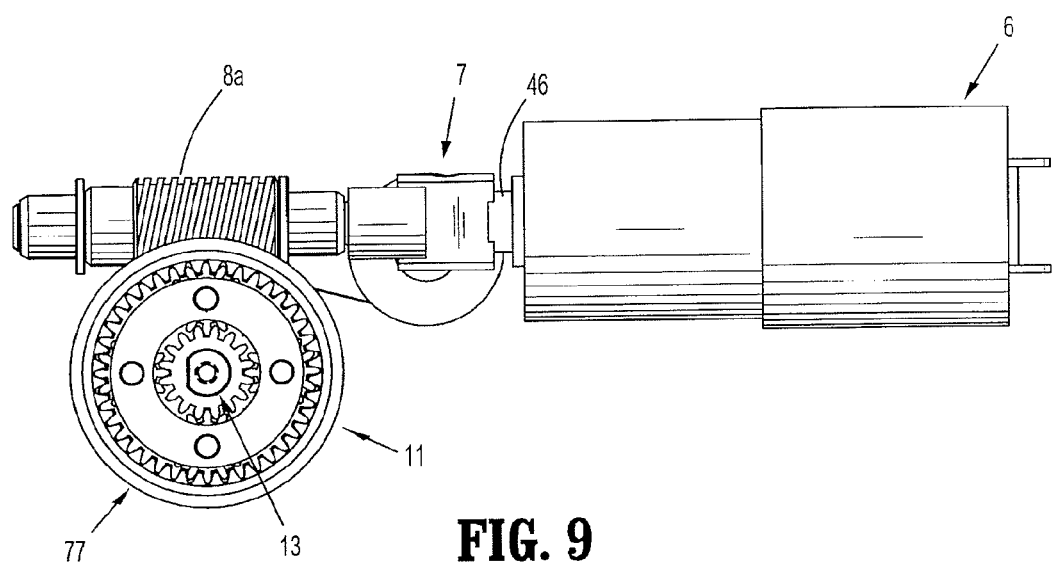
FIG. 9 is a side elevational view of the retraction mechanism of FIG. 6.

In particular, strap 62 is adapted to engage and lock clutch mechanism 11 upon actuation of lever 5, as shown in FIG. 6. In one embodiment, lever 5 includes a trigger 5a, an elongated section 5b, and a hole 5c. Hole 5c is configured to receive a pivot pin 52. Pivot pin 52, or any suitable device, pivotably connects lever 5 with retraction mechanism 3. Lever 5 rotates about pivot pin 52 upon manual manipulation by a user. Lever 5 further includes an opening 5d adapted to receive at least a portion of strap 62. A portion of strap 62 surrounds a ring gear 77 and another portion of strap 62 is operatively connected to lever 5. In one embodiment, a portion of strap 62 is directly connected to the frame of retraction mechanism 3. During operation, a distal translation of trigger 5a of lever 5 moves a portion of strap 62 distally to lock clutch mechanism 11. As lever 5 moves distally, the force exerted by strap 62 along the circumference of ring gear 77 increases and inhibits rotation of ring gear 77. To unlock ring gear 77, a user may return lever 5 to its initial position. Alternatively, lever 5 may return to its initial position under the influence of a biasing device such as a coil spring.

With reference to FIGS. 8-11, clutch mechanism 11 may be composed of a planetary gear system. Clutch mechanism 11 includes a plurality of planet gears 86, a center ring 15, a sun gear 84 and ring gear 77. Sun gear 84 includes teeth 84a and a lumen 54 extending therethrough. Lumen 54 is adapted to receive shaft 13. A portion of shaft 13 is disposed within hollow shaft 78. During operation, hollow shaft 78 rotates around at least a portion of shaft 13. Hollow shaft 78 is disposed in mechanical cooperation with planet gears 86 and, as previously discussed, gear 8b.

Planet gears 86 are positioned around sun gear 84. Therefore, each planet gear 86 is configured to rotate about its center and about the center of sun gear 84. In addition, each planet gear 86 includes a plurality of teeth 86a and a bore 86b. Teeth 86a are configured to mesh with teeth 84a of sun gear 84. Each bore 86b is configured to receive a shaft 60. Shaft 60 connects each planet gear 86 with center ring 15.

Figure 10:
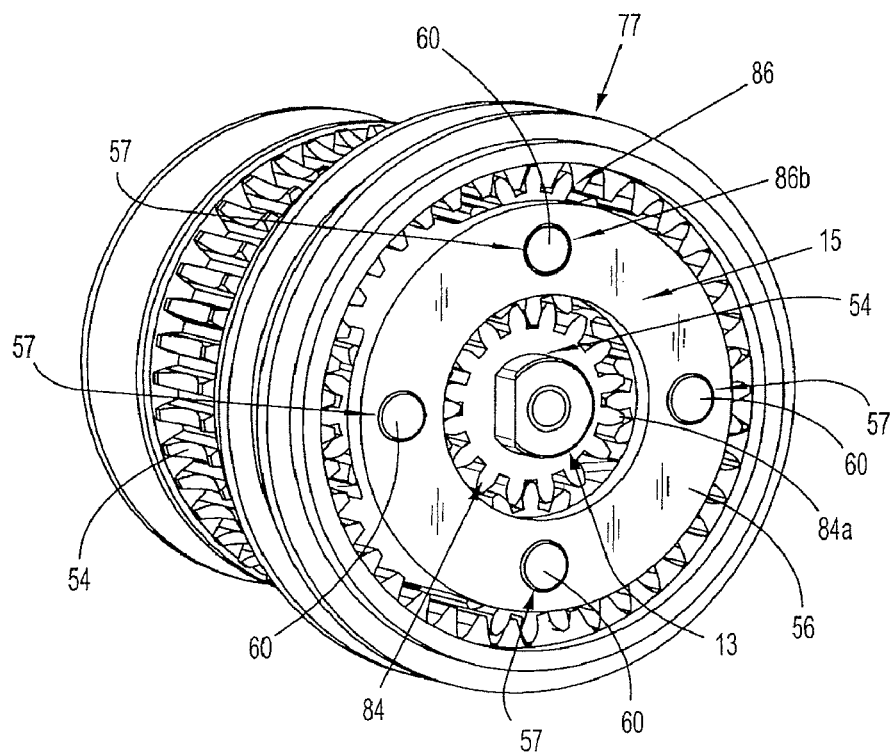
FIG. 10 is a perspective view of a portion of the retraction mechanism of FIG. 6.

Center ring 15 interconnects all planet gears 86 and includes two annular plates 56, 58 disposed in mechanical cooperation with planet gears 16, as shown in FIGS. 10 and 11. Annular plates 56, 58 are each operatively attached to opposing sides of planet gears 86. In particular, annular plate 58 is also operatively coupled to hollow shaft 78. Each annular plate 56, 58 includes a bore 57 adapted to receive shaft 60.

During use, the actuation of lever 5 presses strap 62 around ring gear 77 and immobilizes ring gear 77, thereby placing clutch mechanism 11 in the locked position. The center of ring gear 77 coincides with the center of sun gear 84.

As discussed hereinabove, lumen 54 of sun gear 84 is configured to receive a shaft 13. Shaft 13 is operatively associated with sun gear 84, retraction pulley 9, and spring motor 80. The spring motor 80, FIG. 8, includes a first spool 64, a second spool 66, and a spring 68 interconnecting first and second spools 64, 66. In use, spring motor 80 maintains the tension of flexible member 19 and prevents its entanglement.

Flexible member 19 is operatively secured to retraction pulley 9 as seen in FIG. 11. Retraction pulley 9 has a recess 70 along its circumference. Recess 70 is adapted to receive flexible member 19. Moreover, retraction pulley 9 includes opposing flanges 72, 74. Flanges 72, 74 secure flexible member 19 within recess 70. Flexible member 19 interconnects the retraction pulley 9 and the firing drive 2. Particularly, the second end 19b of flexible member 19 is attached to retraction pulley 9 of retraction mechanism 3, and the first end 19a of flexible member 19 is attached to the proximal end 42b of connector 42.

Retraction mechanism 3 facilitates retraction of the firing drive 2 of a surgical apparatus 10 after firing. In operation, a physician fires surgical apparatus 10 by manually actuating handle assembly 12. The operator may actuate handle assembly 12 with only one hand. Specifically, the user operator manually approximates movable handle member 24 toward stationary handle member 22 to move firing drive 2 distally. The distal translation of firing drive 2 causes anvil assembly 20 to move to the approximated position. In addition, the distal movement of firing drive 2 causes the ejection of the surgical staples disposed in retention slots 18a of cartridge assembly 18. During this process, firing drive 2 translates from a proximal position to a distal position. Since the flexible member 19 is operatively connected to firing drive 2, the distal movement of firing drive 2 also causes the distal translation of flexible member 19. As flexible member 19 moves distally, it unwinds from retraction pulley 9. At this moment, motor 6 is off, clutch 11 is unlocked, and the center ring 15 remains stationary and serves as a ground for the planet gears 86.

Once the surgical apparatus 10 has been fired, the surgeon has to retract drive 2 to its proximal position to reuse it. If manual retraction is desired, the surgeon may move the firing drive 2 to its proximal position through manual manipulation of knobs 32. In particular, the operator may proximally translate knobs 32 with one hand while holding the handle assembly 12 with the other hand. The proximal translation of knobs 32 causes the proximal movement of firing drive 2. Thereafter, surgical apparatus 10 is once again ready for firing.

If powered retraction is desired, an operator may return firing drive 2 to its proximal position by using retraction mechanism 3. The surgeon activates retraction mechanism 3 through lever 5. Particular, the surgeon depresses trigger 5a of lever 5 to activate motor 6 and move clutch mechanism 11 to its locked position. At this instance, strap 62 tightens around ring gear 77 and significantly increases the friction therebetween. Consequently, ring gear 77 is fixed to ground.

The motor 6 drives transmission shaft 46. The rotation of transmission shaft 46 rotates first gear 8a of speed reduction mechanism 8. First gear 8a meshes with second gear 8b. The rotary motion of first gear 8a causes the rotation of second gear 8b. As second gear 8b rotates, hollow shaft 78 rotates and, in turn, causes the corresponding rotation of center ring 15. Consequently, planet gears 86 revolve inside ring gear 77 and around sun gear 84. Planet gears 86 rotate about their center and about the center of sun gear 84. The overall movement of planet gears 86 drives sun gear 84. While sun gear 84 rotates, shaft 13 rotates pulley 9. Pulley 9 rotates in a counterclockwise direction and winds flexible member 19 around it. The rotary motion of pulley 9 also translates flexible member 19 in a proximal direction. The proximal translation of flexible member 19 moves firing drive 2 to its proximal position. Once the process described above is complete, the surgical apparatus is ready for reuse.

During the retraction process, the surgeon may sense that the resistance to retraction is too large for the motor 6 working alone. If this occurs, the surgeon may manually override the retraction mechanism 3. The operator has the option of turning off motor 6 by disengaging lever 5. Then, firing drive 2 of surgical apparatus 10 can be manually returned to its proximal position through knobs 32. The method of using knobs 32 to return firing drive 2 to its proximal position was discussed above.

It will be understood that various modifications may be made to the embodiments disclosed herein. Therefore, the above description should not be construed as limiting, but merely as exemplifications of the embodiments. Those skilled in the art will envision other modifications within the scope and spirit of the claims appended hereto. For instance, surgical apparatus 10 may include sensors to monitor the resistance to retraction by the retraction mechanism 3 to actuate warnings or feedback control of motor 6. Sensors can also be employed to turn motor 6 off when firing drive 2 reaches its proximal position.

What is claimed is:

1. A retraction mechanism for use with a hand held surgical stapling apparatus, comprising:
    a first speed reducing mechanism adapted to be driven by a motor;
    a second speed reducing mechanism having a locked state and an unlocked state, wherein the second speed reducing mechanism is a planetary clutch, wherein the planetary clutch is disposed in mechanical cooperation with the first speed reducing mechanism; and
    a shaft configured to rotate upon activation of the motor when the second speed reducing mechanism is in the locked state, wherein a rotation of the shaft retracts a firing drive of a surgical apparatus.

2. A retraction mechanism for use with a hand held surgical stapling apparatus, comprising:
    a first speed reducing mechanism adapted to be driven by a motor;
    a clutch mechanism incorporating a second speed reducing mechanism having a locked state and an unlocked state, wherein the clutch mechanism is disposed in mechanical cooperation with the first speed reducing mechanism;
    a shaft configured to rotate upon activation of the motor when the second speed reducing mechanism is in the locked state, wherein a rotation of the shaft retracts a firing drive of a surgical apparatus; and
    a pulley coupled to the shaft, the pulley being operatively connected to the firing drive.

3. The retraction mechanism of claim 2, further comprising a flexible member interconnecting the pulley and the firing drive.

4. The retraction mechanism of claim 3, further comprising a spring motor adapted to rotationally bias the pulley.

5. The retraction mechanism of claim 4, wherein the spring motor includes a first spool, a second spool, and a spring interconnecting first and second spools.

6. The retraction mechanism of claim 1, further comprising a hollow shaft interconnecting the first speed reducing mechanism and the planetary clutch.

7. The retraction mechanism of claim 6, wherein the hollow shaft has a bore extending therethrough, the bore being adapted to receive at least a portion of the shaft.

8. The retraction mechanism of claim 1, wherein the first speed reducing mechanism includes a first gear configured to mesh with a second gear.

9. A retraction mechanism for use with a surgical apparatus, comprising:
    a motor disposed in electro-mechanical cooperation with a speed reducing mechanism;
    a planetary clutch operatively coupled to the speed reducing mechanism, the planetary clutch having a locked state and an unlocked state; and
    a firing drive adapted to actuate a surgical tool, the firing drive being adapted to move proximally in response to a rotation of a shaft driven by the planetary clutch while in the locked state, wherein the shaft rotates upon activation of the motor.

10. The retraction mechanism of claim 9, further comprising a pulley coupled to the shaft, the pulley being operatively connected to the firing drive.

11. The retraction mechanism of claim 10, further comprising a flexible member interconnecting the pulley and the firing drive.

12. The retraction mechanism of claim 11, further comprising a spring motor adapted to prevent entanglement of the flexible member, the spring motor being operatively secured to the pulley.

13. The retraction mechanism of claim 12, wherein the spring motor includes a first spool, a second spool, and a spring interconnecting first and second spools.

14. The retraction mechanism of claim 11, further comprising a hollow shaft interconnecting the speed reducing mechanism and the planetary clutch.

15. The retraction mechanism of claim 14, wherein the hollow shaft has a bore extending therethrough, the bore being adapted to receive at least a portion of the shaft.

16. The retraction mechanism of claim 9, wherein the speed reducing mechanism includes a first gear configured to mesh with a second gear.

* * * * *